US010699434B2

(12) United States Patent
Grimm et al.

(10) Patent No.: US 10,699,434 B2
(45) Date of Patent: Jun. 30, 2020

(54) DETERMINATION OF RESULT DATA ON THE BASIS OF MEDICAL MEASUREMENT DATA FROM VARIOUS MEASUREMENTS

(71) Applicant: Siemens Healthcare GmbH, Erlangen (DE)

(72) Inventors: Robert Grimm, Nuremberg (DE); Bernd Schweizer, Ketsch (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 252 days.

(21) Appl. No.: 15/672,347

(22) Filed: Aug. 9, 2017

(65) Prior Publication Data
US 2018/0061077 A1 Mar. 1, 2018

(30) Foreign Application Priority Data

Aug. 23, 2016 (EP) ..................... 16185297

(51) Int. Cl.
*G06T 7/73* (2017.01)
*A61B 5/00* (2006.01)
(Continued)

(52) U.S. Cl.
CPC .................. *G06T 7/73* (2017.01); *A61B 5/00* (2013.01); *A61B 5/0035* (2013.01); *G06F 19/30* (2013.01);
(Continued)

(58) Field of Classification Search
None
See application file for complete search history.

(56) References Cited

U.S. PATENT DOCUMENTS

| 10,191,956 | B2 * | 1/2019 | Bar-Yam | G06F 16/26 |
| 2012/0095322 | A1 * | 4/2012 | Tsekos | A61B 1/00172 |
| | | | | 600/411 |
| 2014/0296697 | A1 * | 10/2014 | Fenchel | A61B 5/0035 |
| | | | | 600/411 |

FOREIGN PATENT DOCUMENTS

| KR | 20100112135 A | 10/2010 |
| WO | WO 2009079650 | 6/2009 |

OTHER PUBLICATIONS

Rata, Mihaela et al.: "Whole body quantitative, multi-parametric characterisation of tumour heterogeneity for response evaluation"; in: Proc. Intl. Soc. Mag. Reson. Med. 21; 2013.
(Continued)

*Primary Examiner* — Jingge Wu
(74) *Attorney, Agent, or Firm* — Harness, Dickey & Pierce, P.L.C.

(57) ABSTRACT

A method is disclosed for determining result data based upon medical measurement data of an examination object. Within the method, a high-dimensional first parameter space is formed, in which measurement values of the various measurements are represented with the aid of value tuples. The measurement values of the various measurements are assigned to a value tuple based on their spatial arrangement in the examination object and/or on their temporal arrangement relative to one another. In the first parameter space, the value tuples are analyzed, using at least one mapping function to at least one further parameter space including a lower dimension than the first parameter space, in order to obtain result data. Furthermore, the result data is output, preferably visualized. In addition, a corresponding device for determining result data is described.

29 Claims, 7 Drawing Sheets

(51) Int. Cl.
| | |
|---|---|
| G06F 19/00 | (2018.01) |
| G16H 50/20 | (2018.01) |
| G16H 30/40 | (2018.01) |
| G16H 10/40 | (2018.01) |
| G16H 50/30 | (2018.01) |
| G06T 7/55 | (2017.01) |
| G06T 7/00 | (2017.01) |
| G06T 15/08 | (2011.01) |

(52) U.S. Cl.
CPC ............... *G06T 7/55* (2017.01); *G06T 7/97* (2017.01); *G06T 15/08* (2013.01); *G16H 10/40* (2018.01); *G16H 30/40* (2018.01); *G16H 50/20* (2018.01); *G16H 50/30* (2018.01); *G06T 2211/40* (2013.01); *G06T 2211/416* (2013.01)

(56) References Cited

OTHER PUBLICATIONS

Korean Office Action and English translation thereof dated Sep. 28, 2018.

Metzger Gregory J. et al.: "Detection of Prostate Cancer: Quantitative Multiparametric MR Imaging Models Developed using Registered Correlative Histopathology", in radiology.rsna.org, vol. 000; No. 0-2016.

Bonekamp Susanne et al.: "Unresectable Hepatocellular Carcinoma: MR Imaging after Intraaterial Therapy, Part II, Response Stratification Using Volumetric Functional Crit-after Intraaterial Therapy", in Radiology: vol. 268, No. 2 (2013); 2013.

Chandarana Hersh et al.: "Diffusion-Weighted Intravoxel Incoherent Motion Imaging of Renal Tumors With Histopathologic Correlation", in: Investigative Radiology, vol. 47, No. 12 (2012); 2012.

Mwangi B et al: "Visualization and unsupervised predictive clustering of high-dimensional multimodal neuroimaging data", Journal of Neuroscience Methods, Bd. 236, pp. 19-25, XP029060419, ISSN: 0165-0270, DOI: 10.1016/J.JNEUMETH.2014.08.001; 2014.

Calhoun V D et al: "A review of group ICA for fMRI data and ICA for joint inference of imaging, genetic, and ERP data", Neuroimage, Bd. 45, Nr. 1, pp. SI63-S172, XP025947909, ISSN: 1053-8119, DOI: 10.1016/J.NEUROIMAGE.2008.10.057; 2009.

Padhani Anwar et al.: "Therapy Monitoring of Skeletal Metastases With Whole-Body Diffusion MRI", in: Journal fo Magn.Reson. Imaging, vol. 39, 1049-1078 (2014); 2014.

Arbabshirani M.R. et al: "Classification of schizophrenia patients based on resting-state functional network connectivity", Frontiers in Neuroscience, Bd. 7, 2013, XP055361958, DOI: 10.3389/fnins.2013.00133; 2013.

Litjens Geert et al.; "Computer-Aided Detection of Prostate Cancer in MRI", in: Transactions on Medical Imaging, vol. 33, No. 6, May 2014; 2014.

Padhani Anwar R., et al: "Therapy Monitoring of Skeletal Metastases With Whole-Body Diffusion MRI"; Journal of MRI, vol. 39: 1049.1078 (2014), Wiley Periodicals, Inc.; 2014.

Moosmann M. et al.: "Joint independent component analysis for simultaneous EEG-fMRI: Principle and simulation", International Journal of Psychophysiology, Elsevier, Amsterdam, NL, Bd. 67, Nr. 3, pp. 212-221, XP022492961, ISSN: 0167-8760, DOI: 10.1016/J.IJPSYCH0.2007.05.016: 2008.

Gatidis Sergios et al.: Combined unsupervised-supervised classification of multiparametric PET/MRI data: application to prostate cancer, in NMR Biomed. 2015, Vo. 28, pp. 914-922; 2015.

Jing Sui et al: "A review of multivariate methods for multimodal fusion of brain imaging data", Journal of Neuroscience Methods, Bd. 204, Nr. 1, pp. 68-81, XP028355490, ISSN: 0165-0270. DOI: 10.1016/J.JNEUMETH.2011.10.031; 2011.

Weinreb Jeffrey et al.: "PI-RADS Prostate Imaging-Reporting and Data System: 2015, Version 2", in: European Urology 69 (2916)16-40, 2015.

Wang, Shijun et al.: "Computer Aided-Diagnosis of Prostate Cancer on Multiparametric MRI: A Technical Review of Current Research", in Hindawi Publishing Corp. Biomed Research International, vol. 2014, Article ID 789561, 11 pages.

Just N. et al.: "Improving tumour heterogeneity MRI assessment with histograms", in : British Journal of Cancer (2014), 111, pp. 2205-2213.

Extended European Search Report dated Apr. 13, 2017.

* cited by examiner

DETERMINATION OF RESULT DATA ON THE BASIS OF MEDICAL MEASUREMENT DATA FROM VARIOUS MEASUREMENTS

PRIORITY STATEMENT

The present application hereby claims priority under 35 U.S.C. § 119 to European patent application number EP 16185297.5 filed Aug. 23, 2016, the entire contents of which are hereby incorporated herein by reference.

FIELD

At least one embodiment of the invention generally relates to a method for determining result data on the basis of medical measurement data of an examination object, the measurement data having been collected in various measurements, preferably with different measurement devices. At least one embodiment of the invention generally relates to a corresponding device for implementing at least one embodiment of method.

BACKGROUND

In medical diagnostics, in particular imaging diagnostics, the possibility of multi-parametric—in particular "multi-modal"—data recording is growing in importance. "Data recording" is understood here to mean the collection of medical measurement data, this referring hereinbelow mainly, but not only, to image data. Measurement data is multi-parametric with regard to different parameters. "Multimodal" here means that the data is acquired with different modalities, i.e. medical measurement devices, in particular medical imaging devices such as MRT (magnetic resonance tomograph), CT (computer tomograph), PET devices (positron emission tomograph), ultrasound systems, etc. Examples of this are multi-parametric magnetic resonance protocols, e.g. additionally in connection with a PET scan. It should be mentioned at this point that multimodal measurement data in this sense is therefore also measurement data which has been generated on combination devices, such as an MRT/PET device, i.e. that the measurement data collected using different measurement principles in a combination device is to be viewed as measurement data from different modalities.

Traditionally, the diagnosis of multi-parametric, in particular multimodal, measurement data and/or images is carried out using a variety of approaches: In one method, the various contrasts or images are displayed sequentially, i.e. the diagnostician reads the images consecutively. An example of this is the detection of a tumor as hyperintense in diffusion imaging high-b-value images and hypointense in diffusion imaging ADC images (ADC=apparent diffusion coefficient). In a further method, the contrasts are shown merged. For example, a T2 contrast of an MRT measurement can be overlaid with the PET scan, the images having previously been registered with one another for this purpose. In particular, the visualization and analysis possibilities have consequently hitherto been restricted as a rule to one-dimensional histograms and two-dimensional scatter plots. For quite specific contrast combinations or combinations of various images (hereinafter also referred to as "parameter maps"), diagnostic parameter combinations are already known, such as for example for the high b-value and the ADC value in tumor diagnoses. It is possible, therefore, to combine the values computationally in advance and then to display and/or analyze the combination value in the form of a parameter map. However, such connections are not generally known for the constantly growing number of possible contrasts. Such procedures are thus restricted to quite specific combinations of values, in principle to such cases where it is already known in advance that specific value combinations are relevant for specific diagnoses.

In clinical reality, there is consequently the risk that it is no longer possible for the increasing amount of available patient data to be analyzed adequately using traditional diagnostic methods. As a result, the potential benefits of multi-parametric imaging are possibly not always being exploited to the optimum.

SUMMARY

At least one embodiment of the present invention creates an alternative method for determining result values on the basis of medical measurement data of an examination object, in particular of a plurality of various measurements, and a corresponding device for this purpose, which can simplify the consideration of a variety of measurement data in diagnostics.

At least one embodiment of the present invention is achieved in a method and at least one embodiment of the present invention is achieved in a device.

At least one embodiment of the method is directed to a method for determining result data on the basis of medical measurement data of an examination object, the measurement data having been collected in various measurements, preferably with different measurement devices. The method of at least one embodiment includes:

formation of a high-dimensional first parameter space in which measurement values of the various measurements are represented with the aid of value tuples, wherein the measurement values of the various measurements are assigned to a value tuple based on their spatial arrangement in the examination object and/or based on their temporal arrangement relative to one another;

analysis of the value tuples in the high-dimensional first parameter space using at least one mapping function to at least one further parameter space which has a lower dimension than the first parameter space in order to obtain result data; and output, preferably visualization, of the result data.

At least one embodiment is directed to a device for determining result data on the basis of medical measurement data of an examination object, the measurement data having been collected in various measurements, preferably with different measurement devices, wherein the device is designed for executing at least the following:

formation of a high-dimensional first parameter space in which measurement values of the various measurements are represented with the aid of value tuples, wherein the measurement values of the various measurements are assigned to a value tuple based on their spatial arrangement in the examination object and/or based on their temporal arrangement relative to one another;

analysis of the value tuples in the high-dimensional first parameter space using at least one mapping function to at least one further parameter space which has a lower dimension than the first parameter space, in order to obtain result data; and output, preferably visualization, of the result data.

At least one embodiment of the present invention is achieved in a non-transitory computer program product having a computer program which can be loaded directly into a storage device of computer unit, with program sections for executing the method of at least one embodiment when the computer program product is executed in the computing unit.

At least one embodiment of the present invention is achieved in a non-transitory computer-readable medium on which program sections which can be read in and executed by a computer unit are stored in order to execute the method of at least one embodiment when the program sections are executed by the computer unit.

Further particularly advantageous designs and further developments of the invention will emerge from the dependent claims and the description hereinbelow, it being possible for the independent claims of one claim category also to be further developed analogously to the dependent claims of another claim category and for the features of various example embodiments to be combined to form new example embodiments.

BRIEF DESCRIPTION OF THE DRAWINGS

The invention will be explained again in greater detail below with reference to the enclosed figures based on example embodiments. The same components are labeled with identical reference numerals in the various figures, in which.

DETAILED DESCRIPTION OF THE EXAMPLE EMBODIMENTS

Figure 1:
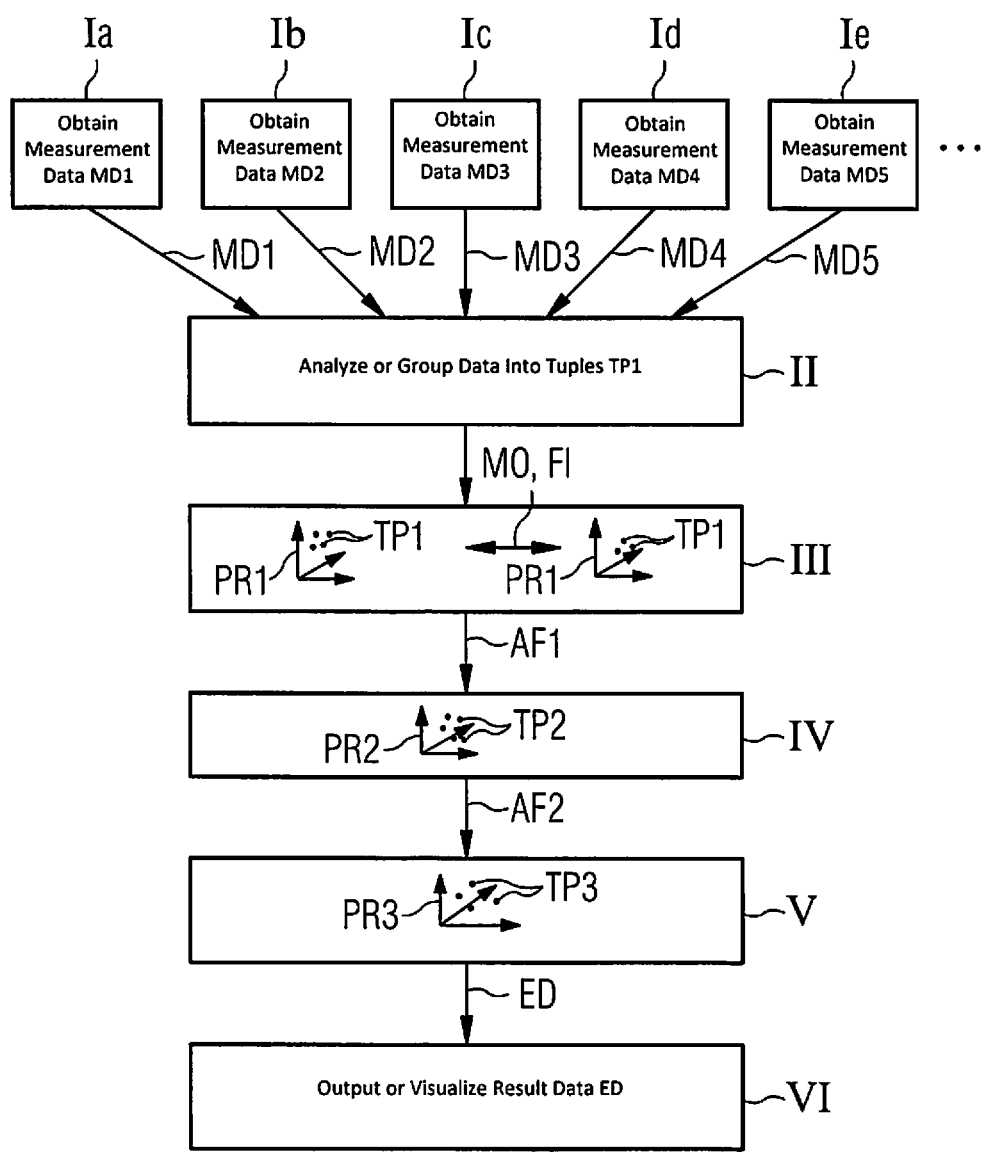
FIG. 1 shows a flowchart of a method according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the method according comprises at least the following:

Firstly, a high-dimensional first parameter space is formed, in which measurement values of the various measurements are represented with the aid of value tuples. Here, the measurement values of the various measurements are assigned to a value tuple based on their spatial arrangement, e.g. picture-element-wise (i.e. voxel-wise or pixel-wise) or region-wise, and/or based on their temporal arrangement relative to one another. In principle and in a most preferred embodiment, a single value tuple can thus be determined for each picture element. It is, however, basically also possible to determine a shared value tuple for a group of picture elements, in particular also for a predefined region of interest in the examination object.

The measurement values which are to be taken into account in the analysis are thus interpreted here as vectors in the high-dimensional parameter space, the vectors being defined by the value tuples. The individual values of the value tuple are in this case the measurement values with regard to a specified measurement parameter, and the measurement parameters thus form the coordinates of the high-dimensional parameter space. Such a high-dimensional parameter space preferably has at least four dimensions, preferably at least five dimensions, but particularly preferably even more dimensions, e.g. quite particularly preferably at least ten dimensions or at least twenty dimensions. Each dimension corresponds here to a parameter to be taken into account.

Once the measurement values are arranged in the form of value tuples or vectors in the high-dimensional first parameter space (defined as explained previously), the value tuples within this first parameter space are analyzed using at least one mapping function to at least one further parameter space which has a lower dimension than the first parameter space. This analysis comprises e.g. analysis with regard to the absolute and/or relative position of the value tuples, their density in the space, etc. The mapping function here can comprise different function types which will be explained in greater detail later. The dimension of the value tuples or vectors is reduced by this mapping function to the second parameter space. The dimensionally reduced value tuples can then be the result data directly or, as will be explained later, can be reduced in their dimension even more by way of further mapping functions.

Ultimately, the result data (combined in this way), i.e. for example, the vectors or value tuples of the lower-dimensioned space, are then output, preferably visualized. Overall, even in the case of a very high-dimensional first parameter space the data is preferably reduced ultimately to a maximum of four dimensions, particularly preferably to a maximum of three dimensions, as three dimensions can be represented graphically relatively well, it being possible for color or other labeling in the three dimensional space to be used as the fourth dimension. In other words, the dimensions are preferably reduced to the extent that the result data can be visualized in such a way that it can readily be understood by the diagnostician. If the first parameter space itself has only four dimensions (which tends to be seldom the case except e.g. in the greatly simplified examples given later), the result data should be reduced at least to three—preferably a maximum of two—dimensions.

A central idea within at least one embodiment of the method resides in interpreting the multi-parametric medical data as high-dimensional parameter space. As mentioned, this measurement data is preferably multi-parametric image data. It can, however, also additionally be laboratory measurement values, anamnesis data or data from previous examination times. In addition, through suitable preprocessing steps, such as e.g. volumetry by automatic organ segmentation, further parameters can be derived from image data which in turn can be interpreted as additional dimensions. As will be shown later, the interpretation of the various measurement data as connected value tuples in a high-dimensional parameter space enables a plurality of analysis options, which in particular can also be performed at least in part automatically, in some cases also fully automatically, which can support the diagnostics considerably. The diagnostics is consequently no longer restricted to generating predefined displayable parameter maps which are then overlaid or have to be viewed sequentially by the diagnostician, which makes the quality of the diagnostics heavily dependent on the experience and knowledge of the diagnostician.

A device according to at least one embodiment of the invention for determining such combined results on the basis of medical measurement data of an examination object from various measurements is designed correspondingly for executing at least one embodiment of the method described above.

The key components of the device according to at least one embodiment of the invention can be embodied here in the form of software components. Basically, however, these components can also be implemented in part, in particular where particularly fast calculations are involved, in the form of software-supported hardware, for example FPGAs or the like. Similarly, the interfaces needed can, for example where only a transfer of data from other software components is involved, be embodied as software interfaces. They can, however, also be embodied as hardware-based interfaces which are controlled by suitable software.

The device according to at least one embodiment of the invention can be implemented e.g. by way of suitable software components on a computer unit which in itself is independent of the modalities or devices for recording the measurement data, for example a workstation, which receives the required measurement data, in particular image data, e.g. via a medical data network such as a radiological information system (RIS) in a practice or clinic, from the respective modalities or devices and/or from a memory in which the data is stored. In principle, the device can, however, also be part of a modality, in particular a combination device such as an MRT/PET device, arranged for example in the controller thereof or in an evaluation station connected directly thereto, in order to perform the method according to at least one embodiment of the invention or parts thereof immediately after the measurement. Accordingly, the collection of the measurement data may on the one hand comprise simply a transfer of the corresponding finished measurement data, such as image data or parameter maps, but may also comprise method steps for the acquisition of raw data and optionally a reconstruction or computation of image data or parameter maps.

A largely software-based implementation has the advantage that workstations or controllers used hitherto can also be upgraded in a simple manner by a software update so as to operate in the manner according to at least one embodiment of the invention. To this extent, the object is also achieved in a corresponding computer program product having a computer program which can be loaded directly into a storage device of a computer unit (for example a workstation of a medical data network), having program sections for executing all the steps of the method according to at least one embodiment of the invention when the program is executed in the computer unit. Such a computer program product may, besides the computer program, optionally comprise additional components such as e.g. documentation and/or additional components, including hardware components such as e.g. hardware keys (dongles, etc.) for using the software.

A non-transitory computer-readable medium, for example a memory stick, a hard disk or another transportable or integral data medium, on which the program sections of the computer program which can be read in and executed by the computer unit are stored, can be used for transport to the computer unit and/or for storage on or in the computer unit. The computer unit may have for this purpose e.g. one or more microprocessors or the like operating together.

Further particularly advantageous designs and further developments of the invention will emerge from the dependent claims and the description hereinbelow, it being possible for the independent claims of one claim category also to be further developed analogously to the dependent claims of another claim category and for the features of various example embodiments to be combined to form new example embodiments.

As already mentioned above, the various measurements may originate in particular from different measurement devices or modalities. In principle, however, in a preferred procedure it is also possible for the various measurements of the same object or of the same region of interest (ROI) to comprise identical measurements, i.e. in particular measurements of the same kind or the same type with the same or approximately identical measurement parameters, which have merely been recorded at different times. These also involve various measurements. An example of this would be the measurement of contrast medium in a specified object such as an organ or tumor tissue at various times, for example consecutively at appropriate time intervals in order to observe the accumulation and/or depletion of contrast medium. The measurement values in the various picture elements, which represent the contrast medium intensity, can then in turn be interpreted as vectors or value tuples.

Here a combination with various other measurements is also possible, i.e. it is possible, for example, for this vector, which comprises the temporal measurements in a certain picture element, to form only a partial vector or partial value tuple within an overall value tuple. Thus, for example, various measurements could also be performed with different devices during contrast medium accumulation and depletion. A value tuple is then assigned for example to a certain picture element and the individual values of the value tuple comprise a partial value tuple, which comprises a first measurement at certain times, and a second partial value tuple, which comprises another measurement at certain times, these partial value tuples being simply linked consecutively to form the overall value tuple. If, for example, two parameter values are each collected at ten points in time, then a value tuple will be produced which comprises a total of twenty values. This value tuple can then be interpreted as a vector in a twenty-dimensional parameter space and analyzed correspondingly within the scope of embodiments of the invention.

As previously mentioned above, there are various mapping function options. The particularly preferred function types include:

Mapping to a color space or a space which comprises a color space (as a subspace), for example an RGB color space, in which three dimensions are defined by the colors red (R), green (G) and blue (B).

Mapping or assignment to discrete classes. Such discrete classes could be e.g. classifications such as the system with the classes PI-RADS 1 to 5 for prostate carcinomas. In other words, using such a mapping function, an—at least partially automatic—classification of the examination object and/or of sub-objects, e.g. of certain regions, can be made. This, as will be shown later with reference to examples, is possible preferably on the basis of the arrangement of the value tuples in one of the parameter spaces.

Mapping to a space with clinically relevant semantic coordinate axes or dimensions, such as for example benign/malign. If for example it is known that a certain parameter combination is with very high probability indicative of malignancy, while another parameter combination is characteristic of benign tissue, a probability of corresponding class affiliation can be indicated for a tissue to be newly classified based on the distance from these reference points.

Mapping to a coordinate system with preferred mathematical characteristics. An example of this would be the use of a principal axis transformation, which is explained in greater detail later.

Integration and/or projection over (pre-)defined areas of the parameter space. An example of this would be the summation of voxels which lie in a certain parameter area, in order in this way to evaluate the volume or the overall "load". If the certain parameter area characterizes tumorous tissue of varying grades, the overall load due to tumorous tissue can be determined e.g. by way of summation. Here, a high volume with low tumor grade can lead to the same overall load as a low volume with high-grade tumor tissue. A further example is the processing of data with a temporal dimension. Here, summation can be used in order to map the area below the time curve or the temporal variability of each voxel, or a projection in order to determine, for example, the temporal minimum or maximum of the parameter.

Similarly, a combination of the above function types and/or further function types is possible in order to form mapping functions which enable mapping from a high-dimensional parameter space to a lower-dimensional parameter space.

In a quite particularly preferred procedure, the dimension reduction occurs in multiple stages. To this end, to obtain the result data, interim result data can preferably initially be determined by a first mapping function from the first parameter space to a second parameter space. This interim result data can then be available e.g. again in the form of value tuples in the second parameter space, i.e. the lower-dimensional parameter space. The interim result data in the second parameter space can then in turn be analyzed, the analysis being carried out again using at least one second mapping function to at least one third parameter space which then has a lower dimension than the second parameter space. This yields, inter alia, the advantage that in each parameter space a suitable analysis can be carried out for the parameter values present there.

Particularly preferably, the first mapping function and the second mapping function comprise different function types or they are based on different analytical principles. For example, it would be possible in a first mapping function firstly for a grouping or clustering of value tuples, which will be explained in greater detail later, to occur and further, based on these clusters, for there to be a principal axis analysis, in order in this way firstly to reduce the dimension of the high-dimensional first parameter space by one or more dimensions. In the second mapping space, which can have coordinate axes which can be given by the principal axes, dividing lines or the like can then in turn be set in order in this way to achieve a further dimensional reduction and to assign certain value tuples to certain areas or characteristics, which, as explained above, corresponds to a further mapping function.

There are consequently different options for analyzing the value tuples in a parameter space. Some particularly key variants are specified below, a combination of the different variants also being possible at any time.

Preferably, the analysis, in particular also an assignment to classes or the like, is carried out taking into account positions of value tuples in a parameter space in relation to a boundary hyperplane of the parameter space. A boundary hyperplane is understood here to be any boundary which divides the parameter space under consideration into areas. These boundary hyperplanes may be linear or planar hyperplanes, such as for example a boundary line in a two-dimensional parameter space or a surface in a three-dimensional parameter space. However, they can also be a hyperplane or hypersurface of any shape, i.e. a bent or curved hyperplane or hypersurface, in particular also a closed hyperplane/hypersurface, for example the surface of a sphere or of a cuboid in a three-dimensional parameter space. Such boundary hyperplanes can simplify for example a characterization or classification of an object (an organ, a structure, a tissue, etc.) by making it possible to establish in a simple manner whether the value tuples which are associated with certain picture elements lie in a certain part of the parameter space, and consequently a statement can be made as to whether the object represented by the picture elements falls within a certain class or can be characterized in a certain way.

As already mentioned above, an analysis is carried out according to a further preferred method such that it comprises an assignment of value tuples to value-tuple groups in order to further examine their properties in isolation, i.e. clustering is carried out. This clustering is preferably carried out fully automatically or semi-automatically, but can also be done manually.

Particularly preferably, an arrangement of a value-tuple group or of multiple value-tuple groups or clusters in the parameter space can be taken into account in the analysis. The analysis of the arrangement here may also cover the location and the extent or shape.

The arrangement of the value-tuple group can preferably also be determined or defined taking into account a collective position of value tuples in the parameter space. Such a collective position can be e.g. the position of a center of gravity of a center point, etc. of the value-tuple group.

Furthermore, the analysis of value tuples or of value-tuple groups can be carried out taking into account a position in relation to at least one reference value tuple, in particular also a reference value-tuple group. The reference value tuples or reference value-tuple groups can be based here on a data collection of reference measurements, for example measurements on certain test groups, e.g. on patients with certain clinical pictures and on healthy test subjects.

Furthermore, the analysis of the value tuples can comprise a segmentation within the parameter space. In the case of such a segmentation, for example areas can be defined manually by being restricted to certain parameter intervals, which can also be viewed as high-dimensional cube segmentation or high-dimensional ellipsoids. Where the parameter space can already easily be represented graphically, it is possible for this also to be carried out manually, a diagnostician separating a certain group of value tuples by drawing boundary lines. Such a segmentation thus corresponds in principle to the specification of boundary hyperplanes within the parameter space described further above.

If a freehand segmentation is to be carried out, this can, however, also be plotted interactively in a two- or three-dimensional visual representation of the parameter space and extruded automatically onto the original parameter space. Such an automatic extrusion can also be replaced by the automatic selection of a most densely occupied parameter area in the non-visible (projected) dimension. This would be analogous to a "correlated cursor" on a spatial-temporal MIP: in this method, a point from the four-dimensional space is assigned automatically by clicking in an image projected onto 2D. The two-dimensional image here shows the spatial and temporal projection, i.e. for each voxel, firstly the highest signal intensity over time is determined and then in this resulting (three-dimensional) temporal MIP the highest signal intensity along the spatial viewing direction is determined. By clicking in this two-dimensional image, firstly the spatial location (x,y,z) in the three-dimensional temporal MIP is determined (position of the maximum along the viewing direction) and then the temporal coordinates (position of the maximum along the time axis for the point (x,y,z).

A further option is semi-automatic or automatic segmentation based on threshold values or by way of the clustering described above, that is e.g. use of cluster detection techniques such as k-means clustering, fuzzy C-means clustering or a regional growth method. Fitting of parametric representations such as e.g. "expectation maximization" for Gaussian mixture models is also possible.

The analysis can also comprise morphological operations and/or filtering. Morphological operations are understood here to refer to, for example, opening operations, closing operations, erosion operations, dilation and/or smoothing, as already used in image processing.

It is also possible to define certain areas through the Boolean combination of sub-areas, e.g. for a region to be defined by the fact that it is affiliated to another region but not to a third region.

In a preferred embodiment, a temporal analysis can also be carried out, which comprises an analysis of the change of value tuples in the parameter space, preferably a temporal shift of individual value tuples or of the arrangement or collective position of value-tuple groups. For example, the shift of the mean value of a cluster over examination times can be a clinical indicator of treatment response.

In a particularly preferred embodiment, the analysis can comprise a machine learning method or machine learning methods can be used in the analysis. Machine learning techniques are particularly appropriate for classification or characterization. This applies particularly to methods using reference value tuples, as, within the scope of classifying or characterizing measurement values or examination objects, new data can be added to the database with each analysis, which—optionally after verification by other examinations—can in turn be used as reference value tuples or reference value—tuple groups (or reference clusters).

In particular, the said high-dimensional, multi-parametric patient data or medical measurement data can also be analyzed with the aid of machine learning techniques in order to identify patterns which may correspond e.g. to classification into clinically relevant classes (e.g. benign, malignant tumor with expected tumor genotype) or to regression into continuous parameter values (e.g. a probability of malignancy; a surrogate for conventional laboratory values). A classifier for predicting the assignment of new patient data can preferably also be trained by way of multi-parametric data from multiple examination objects or patients in which the (clinical) classification is known. I.e. the data is used, as explained above, as reference data for the subsequent analyses. At the same time, a decision rule of the classifier can preferably also be extracted in order then to function in future as a decision-making criterion in manual image-based diagnostics. For example, decision trees for classifications can be learnt automatically. Artificial neural networks can also be used for the machine learning techniques.

In the graphical representation of the parameter space, higher dimensions can also be included by way of extended visualization techniques such as e.g. mapping to a color scale or description by way of vectors/glyphs. For example, multiple examination times can be represented in different colors in a 2D scatter plot or the shift of a point cloud (cluster) can be represented by a vector in the scatter plot.

Preferably, the visualization of the result data comprises a labeling, particularly preferably in color, of picture elements and/or regions in a spatial domain representation, i.e. in an anatomical image of the examination object. The labeling can be carried out here depending on a result of the analysis of the value tuples in the first and/or a further parameter space, in particular also of a possible temporal analysis. In other words, the high-dimensional parameter values or parameter values projected onto a low-dimensional space can be merged with the anatomical image data by way of back-mapping or extended back-mapping for visualization. In addition to histogram coloring, semantic classes such as e.g. benign or malignant regions or probability values for affiliation to a certain class can also be visualized by labeling, in particular in color. In particular, the temporal analysis can also—as already mentioned above—be visualized by colors or vectors, e.g. a temporal shift as a vector in the scatter plot.

Particularly preferably, in the visualization of multi-parametric data, models or results known from previous studies can also be plotted in the parameter spaces as references. For example, manual or (semi-)automatically defined parameter areas such as high-dimensional rectangles, ellipsoids or hyperplanes or other decision boundaries can be overlaid on the data graphically.

In summary, the following advantages are thus achieved by the method according to an embodiment of the invention:
reduction of data dimensionality,
enhanced visualization techniques and back-mapping,
segmentation techniques for certain areas in high-dimensional parameter spaces,
regression and classification techniques for the automatic analysis of multi-parametric data,
extraction of new decision rules for conventional image-based diagnostics.

The potential of the processing of multi-parametric measurement data in accordance with an embodiment of the invention can consequently be exploited for improved diagnosis and treatment and furthermore then also for cost savings and for optimized examination and treatment pathways.

In the example of the process flow shown in FIG. 1, measurement data MD1, MD2, MD3, MD4, MD5 from different measurements Ia, Ib, Ic, Id, Ie is firstly transferred in method step II. These measurements Ia, Ib, Ic, Id, Ie may for example be performed on different devices, e.g. in method step Ia on an MRT device, in method step Ib on a CT device, in method step Ic on an ultrasound device, in a method step Id on a PET device, and in a method step Ie, the transfer or input of laboratory values such as for example PSA values or other blood values is involved, for example. In principle, further devices or measurement data such as ECG data etc. can also be added. Equally, the different measurements can however also be performed on one and the same device, different parameters being evaluated, for example different contrasts etc. in an MRT measurement but also with the same or very similar parameters but at different times and/or under different conditions such as with or without contrast media.

In many cases, the measurement data MD1, MD2, MD3, MD4, MD5 concerned is image data or parameter maps. This may be two-dimensional data, three-dimensional data such as e.g. volume data or even four-dimensional data, for example volume data that was recorded at certain time intervals, so time represents the fourth dimension.

In method step II, a preliminary analysis or grouping of the data into value tuples TP1 for a high-dimensional parameter space PR1 can then be carried out, i.e. the measurement values can be compiled into vectors, one vector, for example, containing the measurement data of a picture element (pixel or voxel), optionally also at different times. Equally, however, one value tuple may also comprise a value at different times for a group of picture elements, optionally also for a certain organ or a certain region, respectively.

The high-dimensional first parameter space PR1, in which the value tuple TP1 which is formed from the individual measurement values of the measurement data MD1, MD2, MD3, MD4, MD5, is then analyzed in step III. This analysis may, as is shown schematically, also comprise data filtering FI and/or morphological operations MO, i.e. a type of pre-processing takes place within the high-dimensional first parameter space PR1.

However, the analysis in the high-dimensional parameter space PR1 comprises in particular a mapping with the aid of a first mapping function AF1 in a lower-dimensional parameter space PR2. For example, a parameter space PR1 with more than twenty dimensions can be mapped here to a parameter space PR2 with for example five or six dimensions. This will depend only on the choice of mapping function AF1. Examples of this will be given later.

In method step IV, an analysis of the value tuples TP2 obtained by the first mapping function AF1 in the second, lower-dimensional parameter space PR2 takes place. Here, the same analytical methods can be used that were used in step III in the higher-dimensional parameter space PR1, adapted appropriately to the lower dimensions, of course. As a rule, however, the analytical methods involved are different.

For example, in the first stage in step III clustering into value-tuple groups with regard to certain dimensions of the first parameter space PR1 could be carried out. The mapping function AF1 can then be chosen such that a number of parameter values which precisely these dimensions with regard to which the clustering was carried out, is replaced simply by one parameter value which represents the assignment to one of the clusters. In this way a considerable dimensional reduction can be achieved. In the subsequent stage, a subclassification or the like can then be carried out again in the analysis in the lower-dimensional parameter space PR2. To this end, it can, for example, be checked where the new reduced value tuples TP2 are located in relation to a boundary hyperplane. In principle, in this further analysis in the second parameter space PR2, a mapping is also carried out by way of a (further) mapping function AF2 to a third, even lower-dimensional parameter space PR3, in which the value tuples are then represented by corresponding value tuples TP3. In the further parameter space PR3, any analysis and further reduction can then be carried out again, preferably also with a mapping function, to a further even lower-dimensional parameter space.

This variant is not shown in FIG. 1, but here a stage is reached as early as step V in which during the analysis in the last parameter space PR3 the result data ED is determined immediately, which is then output or visualized in step VI. In principle, however, even more than three stages would also be possible.

An output or visualization may for example comprise a back-mapping to a spatial domain of the examination object, i.e. for example overlaying in an anatomical image, etc. In addition, this result data may, however, also comprise only the output of an individual classification or characterization of the examination object, i.e. e.g. of the patient or of an organ or of a certain tissue area of the patient. At this point, it is pointed out that in the case of a classification the result data ED is usually only diagnostic proposals which generally can or have to be confirmed by the diagnostician. Likewise, it is also possible for the classification or characterization to be made with information about probabilities with which the examination object or organ or tissue parts correspond to this classification or characterization.

Figure 12:
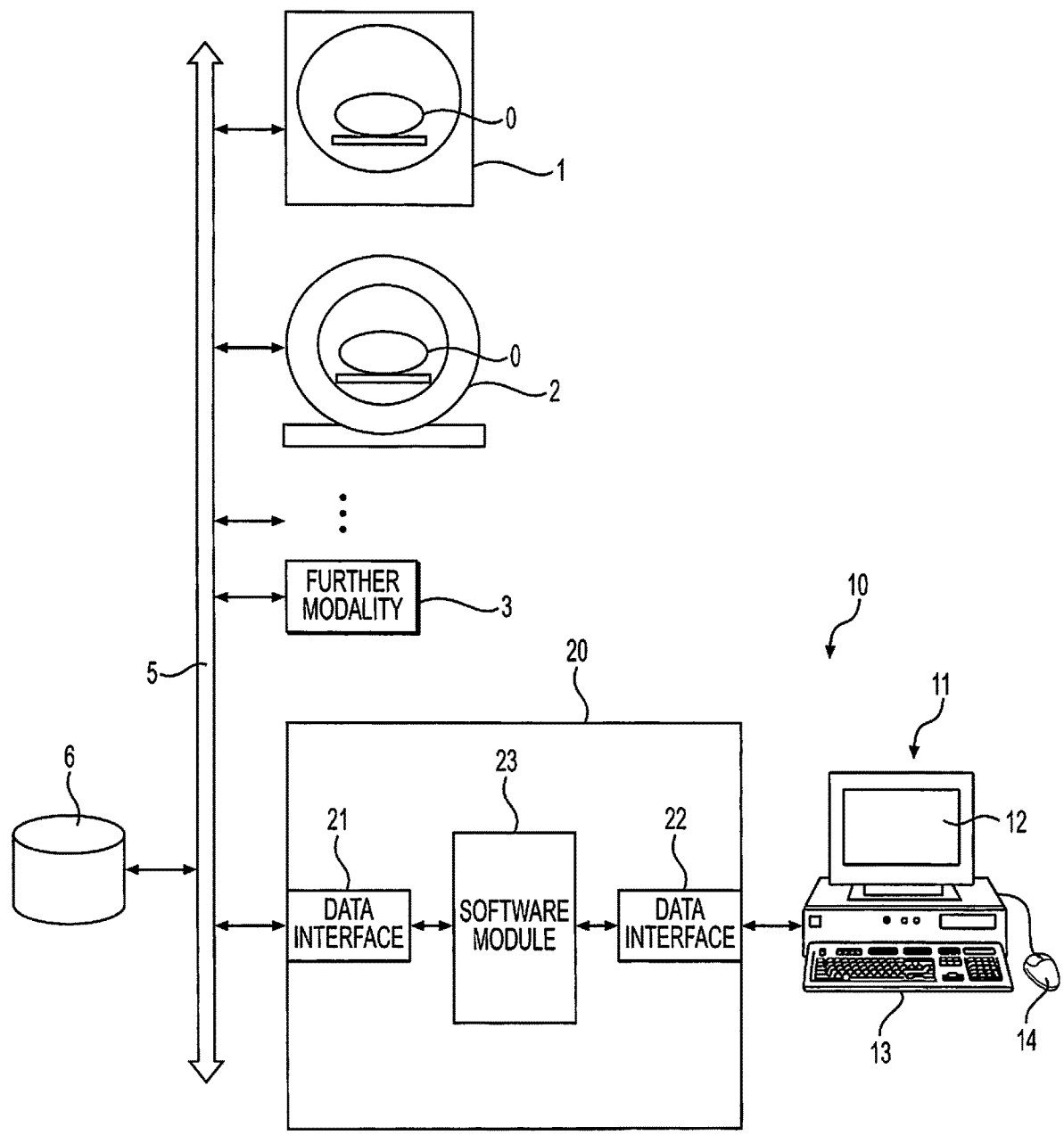
FIG. 12 shows a schematic representation of a medical data network with multiple modalities connected thereto and a device connected thereto for determining result data on the basis of medical measurement data from various measurements according to an example embodiment of the invention.

FIG. 12 shows schematically a device 10 with which such a method can be implemented. Shown here is a medical network, for example a radiological information system (RIS), in which various devices are connected to one another via a data bus 5. The present case concerns firstly modalities 1, 2, 3, on which measurements are carried out on the examination object O and from which measurement data can be acquired, a mass storage device 6, for filing measurement data, in particular raw data, image data, etc., and the device 10 according to an embodiment of the invention for determining the result data based on the medical measurement data. Further devices, in particular also an interface to an external network, for example the Internet etc., can additionally be connected to this network or to the data bus 5.

In the example shown, one of the modalities 1 is a combined MRT-PET device 1. Another modality 2 is a computer tomograph 1. A further modality 3, for example an ultrasound device, an X-ray device, etc., is shown only symbolically. A further interface for the transfer of laboratory values, etc. could also be provided here in order additionally to transfer and use these values within the method.

The device 10 according to an embodiment of the invention comprises here firstly a computer unit 20, which is connected via a data interface 21 to the data bus 5 and via a further data interface 22 to a terminal 11 for operating the device 10. The computing unit 20 also comprises a corresponding software module 23 containing the required software components for executing the data processing measures and calculations for implementing the method according to an embodiment of the invention. The computer unit 20 usually comprises furthermore a suitable storage device (not shown here) (hard disk(s), RAM, etc.), on which the necessary software components are stored.

The terminal 11 comprises an output unit 12, symbolized here by a simple screen, and input units, such as for example a keyboard 13 and/or a pointing device 14, symbolized here by a mouse. Of course, the screen 12 can also take the form of a touchscreen or the like. The entire device 10, i.e. the computer unit 20 together with the terminal 11 or the user interface 11, can be implemented for example in the form of a customary workstation for diagnostics in a medical data network.

Via the terminal, the diagnostician can select certain data, display this and/or with the aid of a graphical user interface, namely screen 12 and keyboard 13 and mouse 14 or other appropriate tools, optionally place labels and boundary lines and perform segmentations, etc., as will be explained below. Likewise, commands can be given to store data, to configure the computing unit 20 with regard to the analytical methods desired or the dimensions of the parameter spaces, etc. In other words, all user actions in respect of operations to be supported or initiated by a user within the scope of the method can be carried out with the aid of this terminal, for example.

The basic procedure with regard to certain analytical techniques, mapping functions and visualization methods will be explained below with reference to further figures with the aid of simple examples. Where figures have been used for this purpose, the examples given are limited to three dimensions for reasons of representability, but these operations can also as a rule be implemented in the high-dimensional parameter spaces.

Figure 2:
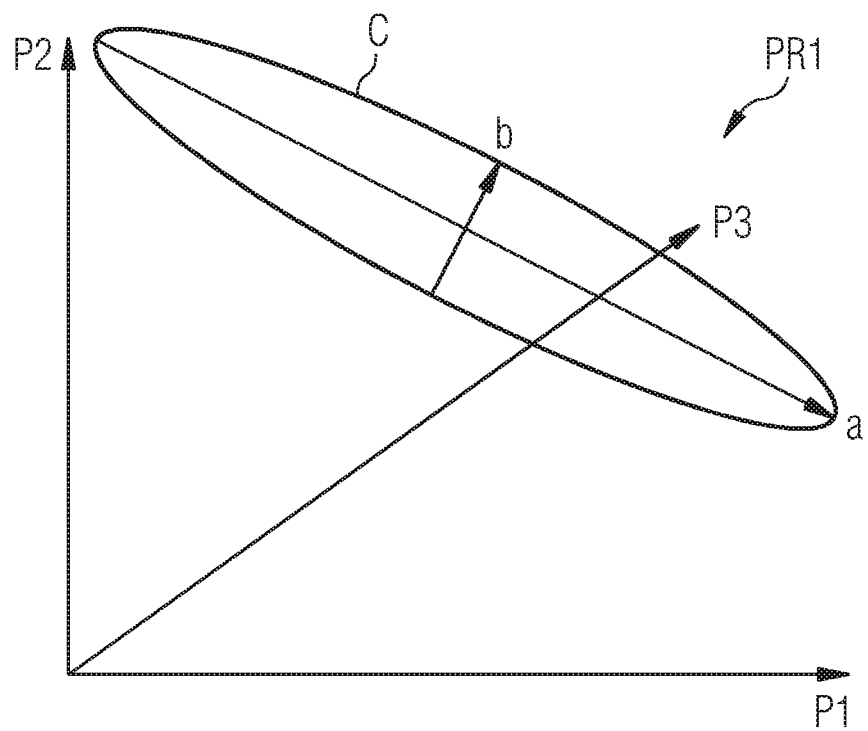
FIG. 2 shows a schematic representation of an example of a point cloud in three parameters and principal axes determined for these.
Figure 3:
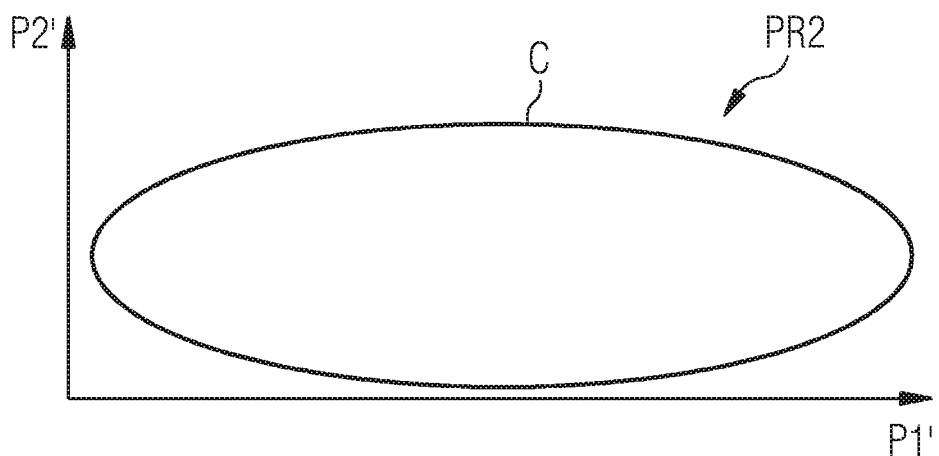
FIG. 3 shows a schematic representation of the point cloud from FIG. 2 transformed onto the principal axes with reduced dimensionality.

FIGS. 2 and 3, for example, show a method by which a reduction of data dimensionality can be carried out with the aid of a principal axis transformation. FIG. 2 shows schematically an adapted envelope of a point cloud (itself not shown), i.e. for example a cluster of value tuples, in a three-dimensional space with the coordinate axes P1, P2, P3. These coordinate axes P1, P2, P3 are the parameters which are represented by the corresponding parameter value in the value tuple. It will be shown later with the aid of FIG. 6 how such a clustering of value tuples can be carried out.

In the three-dimensional view shown here in FIG. 2, such a cluster or the point cloud of interest can be recorded visually. However, for quantification, all three output parameters or coordinates P1, P2, P3 must also be examined here. Often, the data is restricted to low-dimensional subspaces, such as in the example below a planar or virtually planar ellipse. The principal axes a, b and suitable coordinates can be determined in this three-dimensional space by way of a conventional principal axis transformation. The point cloud or the cluster C can then be represented accordingly in a parameter space PR2 reduced to two dimensions with the coordinate axes P1', P2', one coordinate axis P1' running in the direction of the one principal axis a and the other coordinate axis P2' running in the direction of the other principal axis b of the ellipse. In the case of a reduction from three to two dimensions, this can still easily be represented, as in FIGS. 2 and 3. However, it is clear that this basic principle can be applied to considerably higher-dimensional spaces. Due to the reduction of dimensionality, the point cloud can then be analyzed substantially more easily by way of user-friendly methods, as in the present case e.g. two-dimensional definition of regions of interest, stipulation of threshold values, etc., than would have been possible in the originally higher-dimensional parameter space.

Figure 4:
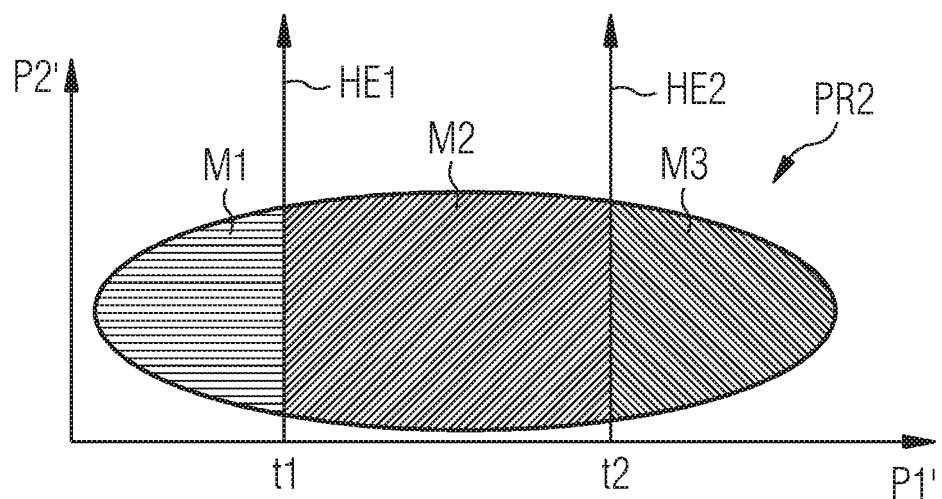
FIG. 4 shows a simplified example of a segmentation of three regions in the reduced parameter space according to FIG. 3.

This will be illustrated with reference to FIG. 4 in a simple example below. Here, the point cloud (cluster) from FIG. 4 is divided with the aid of two threshold values t1 and t2 into three areas. These threshold values t1, t2 here form virtual hyperplanes HE1, HE2 of the two-dimensional parameter space PR2. The value tuples can thus be assigned to different regions in the parameter space, here all value tuples below the threshold t1 of the parameter P1', all value tuples between the thresholds t1 and t2 with regard to the parameter P1' and all values above the threshold t2 with regard to the parameter P1'. The setting of the threshold values t1, t2 or of the hyperplanes HE1, HE2 is of course usefully carried out in accordance with a particular medical relevance or statement, for example "presumed healthy tissue", "presumed tissue of a malignant tumor" or "presumed tissue of a benign tumor". This principle can also be applied to any higher-dimensional space.

Figure 5:
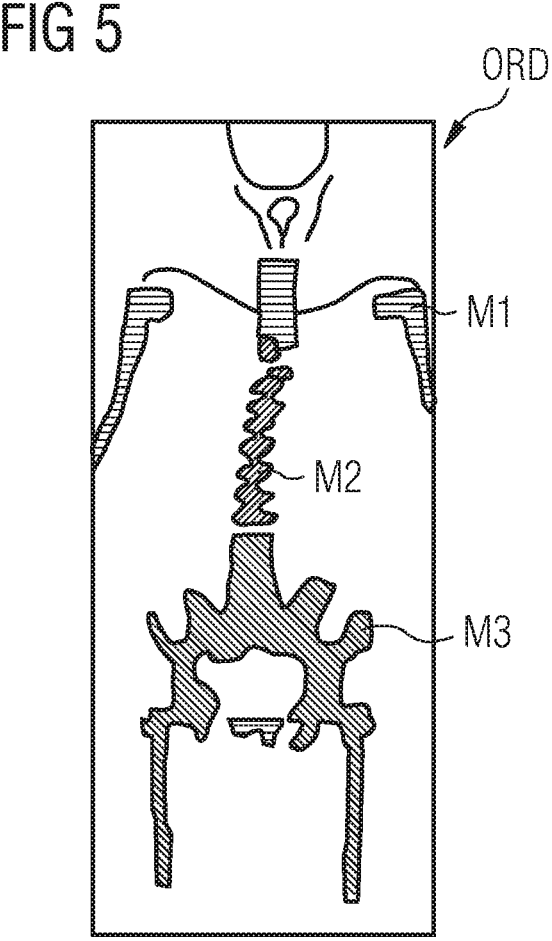
FIG. 5 shows a simplified example of a labeling of picture elements in an anatomical image or a spatial domain representation of the examination object according to their regional affiliation to the regions in FIG. 4 (back-mapping to the morphological source voxels)

Back-mapping of the regional affiliation of value tuples, e.g. by color coding, to the original morphological voxels, as shown in FIG. 5, is then possible. In other words, a color value is assigned here to each value tuple which stands for or represents a particular picture element of the original image, based on the regional affiliation in the space PR2 as shown in FIG. 4, and this color value is then used to label the corresponding picture element, i.e. pixel or voxel, in the spatial domain representation ORD. Thanks to these colored labels M1, M2, M3, the diagnostician can thus immediately recognize in the spatial domain representation ORD which region or which classes the picture elements concerned within the parameter space PR2 in FIG. 4 are to be assigned to. The labeling can be carried out in particular also by overlaying a mask containing corresponding labeling of the picture elements with an anatomical image.

Figure 6:
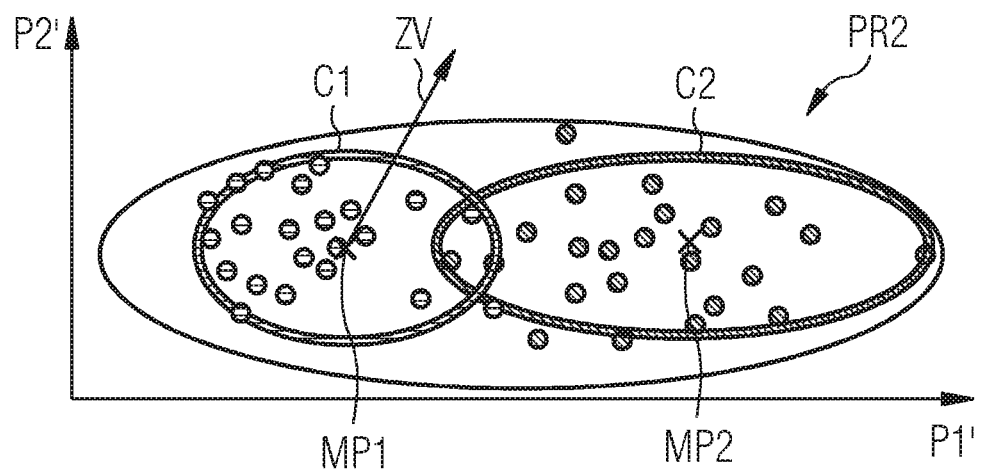
FIG. 6 shows a simplified example of a determination of subgroups by way of automatic clustering.

FIG. 6 shows another way in which, instead of threshold values being set as in FIG. 4, a point cloud could be analyzed in dimensionally reduced space. As an example, it is shown here how, with the aid of automatic clustering algorithms, sub-groups or sub-clusters C1, C2 are in turn defined within the point cloud or the large cluster. For these clusters C1, C2 or sub-clusters C1, C2, as for any cluster, collective marker points can also be defined, here e.g. center points MP1, MP2 or centers of gravity of the clusters C1, C2 or other "cluster centers".

Where a temporal analysis is carried out, i.e. in a further dimension the individual value tuples can be arranged over time within the parameter spaces under consideration in each case (for example, simply by adding a time axis), after the temporal behavior has been evaluated, a shift of such a cluster C1, C2 in the space can also be labeled or displayed. Such a temporal shift ZV can also be represented by a vector, showing the direction in which, for example, the collective point, here the center point MP1 of a cluster C1, moves with time.

A display of the behavior over time is often useful, as the temporal variance can also contain medically relevant information. This can particularly be the case, for example, where different measurements at more widely spaced time intervals are involved, e.g. as part of progress or follow-up measurements for checking the success of a treatment. In this way, with the aid of a vector for the temporal shift ZV of a cluster C1, it is possible to visualize extremely well whether a treatment is working or not.

In particular, it is also possible to use the detected cluster centers in a patient population to determine for a new patient case a probability of a particular class affiliation, i.e. the analyses carried out here or the collective values or centers (or center points, centers of gravity, etc.) of clusters determined in the process can for example then be used as reference values in order then to be able, using these in analyses of the measurement values of other patients, to perform a classification or characterization of tissue, organs, etc.

Furthermore, it is also possible to extract new decision rules for conventional image-based diagnostics using the method according to an embodiment of the invention. If, within the scope of the method according to an embodiment of the invention, it transpires e.g. that a searched-for sub-group can also be adequately precisely differentiated in the original parameter space by way of simple threshold value formation, this result can then be translated into an image-based diagnostics rule.

Figure 7:
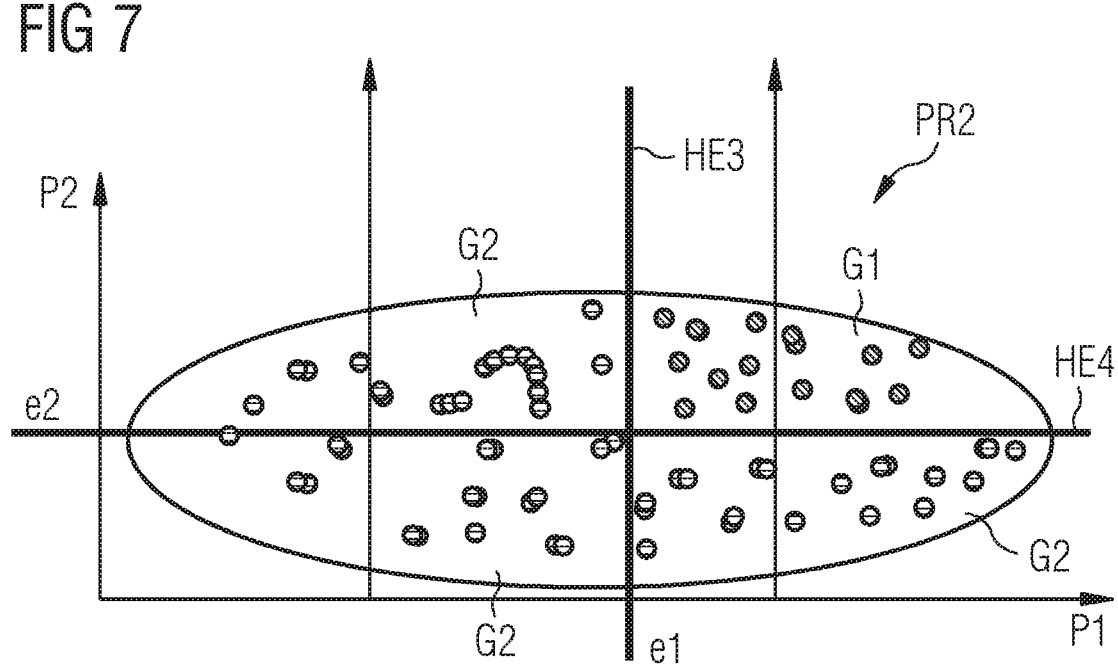
FIG. 7 shows a simplified example of a possible image-based diagnosis based on threshold values (boundary lines)

A particularly simple example is shown here with reference to FIG. 7. It has been established here within the scope of further analyses that if a voxel intensity in relation to the parameter P1 lies below a limit value e1, i.e. to the left of a hyperplane HE3 in the image, and if at the same time the voxel intensity in relation to the parameter P2 is greater than a limit value e2, i.e. lies above a hyperplane HE4 in the image, this voxel belongs to a group G1, for example to healthy tissue. Otherwise, it belongs to the group G2, which indicates a tissue with a lesion.

Further, more specific example embodiments of the method according to an embodiment of the invention will be explained in simplified form below.

Figure 8:
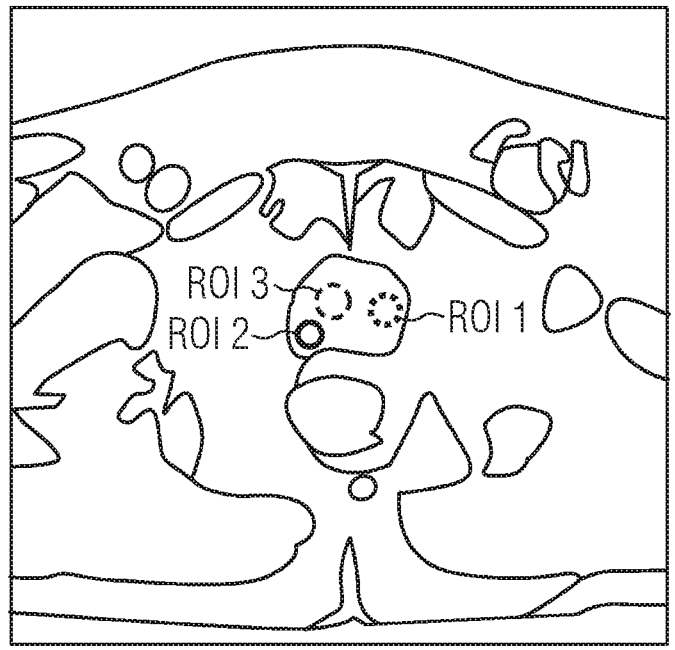
FIG. 8 shows a schematic representation of an example of labeled regions of interest (ROIs) in a magnetic resonance sectional image through a prostate.
Figure 9:
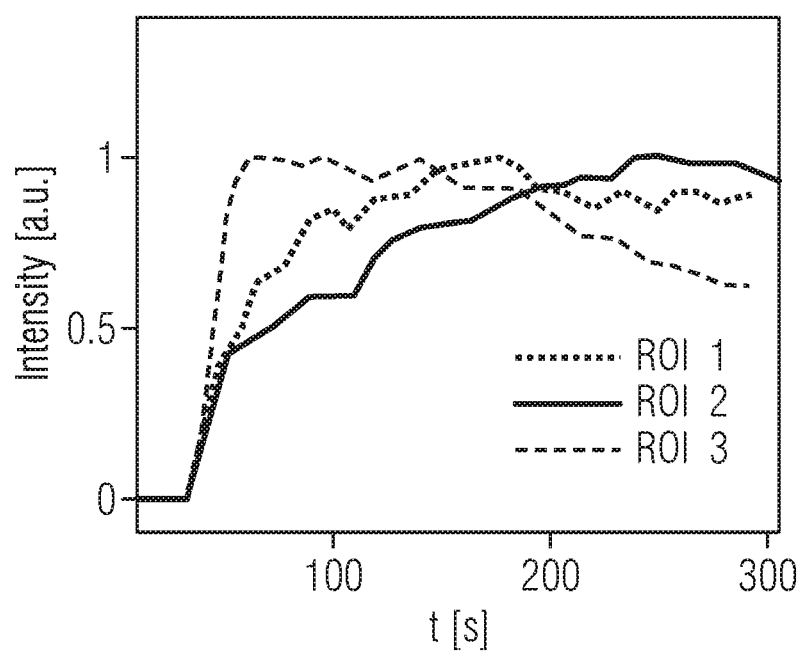
FIG. 9 shows an example of different time curves in a dynamic contrast-medium magnetic resonance measurement of the prostate in the regions of interest labeled in FIG. 8.

Example 1: Differentiation Between Healthy and Diseased Tissue by Way of Dynamic Contrast-Medium-Assisted Perfusion MRT In this example, which is explained with the aid of FIGS. 8 to 10, the measurements concerned are dynamic contrast-medium-assisted perfusion MRT measurements. In this case, during administration of contrast medium, multiple, typically four to fifty, volumes are acquired. The accumulation behavior of the contrast medium differs between different tissue types and different organs and consequently also permits differentiation between healthy and diseased tissue (such as tumors). In this regard, different regions of interest ROI1, ROI2, ROI3 in the prostate are shown schematically in FIG. 8. FIG. 9 shows in this regard the different time curves for such a dynamic contrast-medium-assisted MRT in the prostate. In this regard, the contrast medium accumulation curves (intensity in arbitrary units [a. u.]) over time t (in s) are shown respectively, a mean value being used in each case for the different regions ROI1, ROI2, ROI3 from FIG. 9. In the literature or in particular product solutions obtainable on the market, different approaches to the analysis of such contrast-medium-assisted dynamics exist. For example, the increase in the contrast-medium wash-in or wash-out can be calculated in the time curve of each voxel.

According to an embodiment of the invention, the curve of the image intensity of each individual picture element, i.e. voxel or pixel, over time can be interpreted as a parameter vector. With p recorded time phases for each picture element, this gives a p-dimensional vector in a p-dimensional parameter space. Within the scope of the present invention, such a p-dimensional parameter space can now be analyzed and, with the aid of mapping functions, processed such that an efficient representation or use is possible. In this connection it is explicitly pointed out that the analysis of dynamic contrast-medium-assisted perfusion MRT data can also be carried out analogously for diffusion-weighted MRT data or general multi-parametric imaging data.

For example, within the scope of training measurements or the like, example signal curves from patients with e.g. histopathologically known tissue characteristics can be generated or made available for various classes, such as e.g. k=5 classes "tumor", "necrosis", "healthy organ 1 tissue", "healthy organ 2 tissue", "vessel". With the aid of this reference data, the probability of affiliation to each of the five classes mentioned can then be estimated in the p-dimensional parameter space for each signal curve with unknown tissue characteristic. By way of such an assignment function, the dimension of the parameter space can consequently be reduced from p to k, i.e. here five classes. This dimensional reduction is performed data-independently, as the reference curves originate from a library which was created previously.

Alternatively, however, data-dependent dimensional reductions can also be carried out analogously, with similar time curves from a study being grouped automatically and assigned to clusters, without external reference curves necessarily being used in the process. Something of this kind can be implemented in an algorithm using k-nearest neighbor classifications.

An alternative data-dependent technique for dimensional reduction is also again a principal axis transformation here. The data vector for each spatial point could be mapped onto a new basis in which the greatest variation is aggregated in the first dimensions. This also provides the option of usefully reducing the dimensionality by discarding the higher dimensions. Assuming continuous class affiliation probabilities, each picture element can also be assigned to a particular class.

Figure 10:
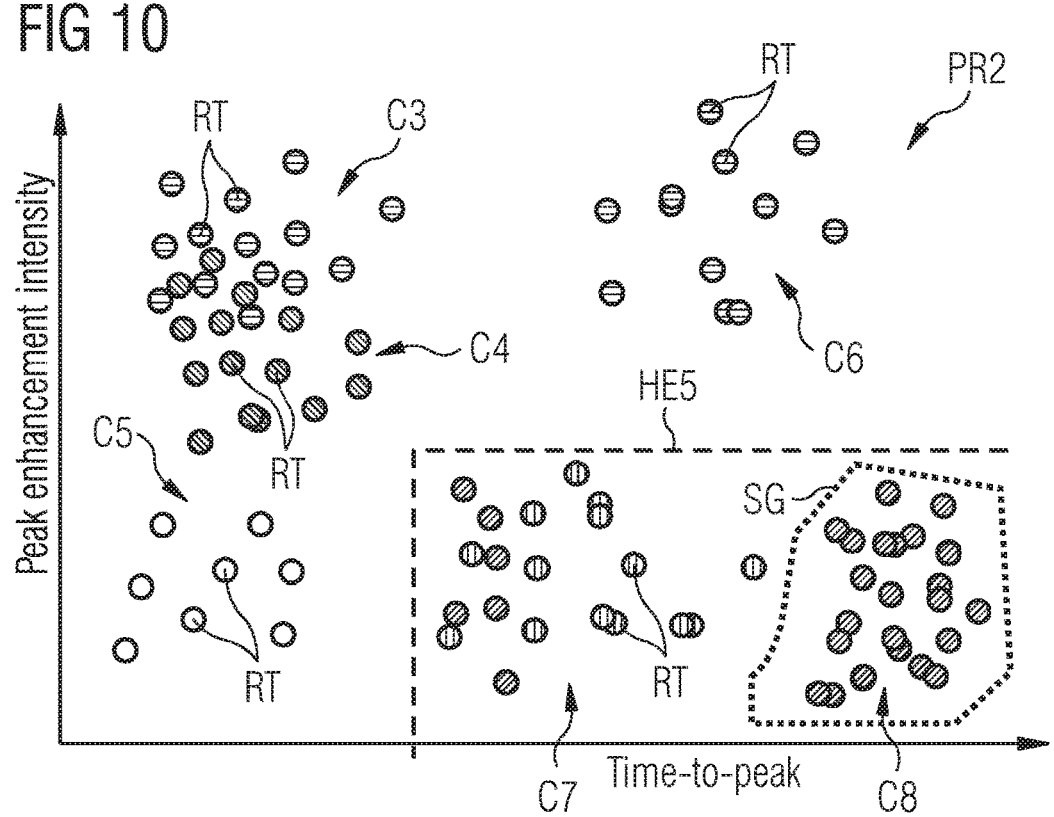
FIG. 10 shows an example of clustering and segmentation with the aid of boundary lines in a two-dimensional parameter space for measurement values from a measurement according to FIG. 9.

Furthermore, each picture element can be visualized relative to a different, low-dimensional, clearer basis. In the diagram shown in FIG. 10, the maximum contrast-medium intensity (peak enhancement intensity) and the temporal position of this maximum (time to peak) are used as a basis for a representable vector space (FIG. 10 is only a schematic representation with arbitrary axis scaling; the clusters plotted are also arbitrary here and chosen as such only for reasons of clarity). Class affiliation to a particular class can be signaled by a color (or as in FIG. 10 by different symbols). Thus, in this diagram, a total of eight different clusters form, a cluster C3 for picture elements which represent the aorta, a cluster C4, which comprises tumor tissue, a cluster C5 for healthy prostate tissue, a cluster C6 for healthy bladder tissue and two clusters C7, C8, which both represent necrotic tissue, as they are located in a region in this parameter space PR, which is sectioned off from the remaining area of the parameter space PR2 by a kinked hyperplane HE5 or a boundary line. For the clustering, reference value tuples RT from previous studies can be used (by way of example, a few reference value tuples RT are symbolized here for different clusters). The hyperplane HE5 may also be known, for example, from previous studies. Here, there may be one or more decision boundaries, which may be justified here by amongst other things, for example, the recognition that necrotic tissue typically exhibits a very slow contrast-medium wash-in and a very low peak enhancement. As support, such decision boundaries can be visualized with the actual data points.

Conversely, as also shown in FIG. 10, visually identifiable decision boundaries can also be translated back into simple conventional decision rules. In the present case, for example, if the "time to peak" parameter is greater than the threshold defined by the hyperplane HE5 and the "peak enhancement intensity" parameter is lower than the threshold defined by the hyperplane HE5, the tissue is most probably "necrotic".

In addition, known cluster centers or corresponding probability density distributions can be displayed. In the example in FIG. 10, it can be seen that necrotic tissue is grouped in two sub-clusters C7, C8 which are possibly caused by different tissue processes. In order to check a possible spatial connection, the diagnostician can select a portion of the picture elements or value tuples labeled as necrotic in the parameter space. This is possible e.g. by free-hand segmentation SG with the aid of the user interface or the terminal. Such a freehand segmentation SG is symbolized in FIG. 10 by the dotted line.

The value tuples or picture elements selected by this can then in turn be overlaid in a back-mapping process with a suitable anatomical image. In principle, however, back-mapping of all the value tuples or picture elements can be carried out simultaneously, each point being color-coded or encoded by a symbol according to its class affiliation.

In the specific methods mentioned previously, data analysis with a machine learning method is again also possible. For accurate clinical diagnosis and treatment, specific pathological findings or biomarkers (blood serum values, etc.) are often crucial. Through data analysis with the aid of a machine-learning method, computer systems can be trained to carry out automatic mapping of multi-parametric medical image data onto such surrogate biomarkers, which in this case are synthetic. For example, such a system can, through automatic analysis of prostate cancer patient datasets with given PSA values and histopathological findings (biopsy Gleason score) as well as corresponding multi-parametric MRT imaging, learn a correlation between the image parameters and the Gleason score or the PSA value. This correlation model can subsequently be used in order to predict a Gleason-score value for new patients based on image data, without a biopsy having to be carried out.

Example 2: Assessment of the Therapeutic Success of Intra-Arterial Therapy by Way of MRT Measurements Particularly in the case of intra-arterial therapies for liver tumors and similar, one aim is to establish early through the detection of changes in MRT progress monitoring whether the therapy is working or should be replaced by alternative therapies. The therapy response can, for example, be classified as "responder", "semi-responder" and "non-responder". To do this, various MR contrasts, including contrast-medium-assisted liver dynamics, are acquired before and after the therapy, typically approx. twelve volumes in each case.

In the literature and in practice, different approaches to the analysis of changes exist. For example, the average ADC value or average venous enhancement (VE) for the target region, i.e. the tumor, can be determined at any time for this purpose. It would be possible here to use simple threshold values in order to evaluate the therapy response based on changes in the average ADC value and the average VE value.

Within the scope of the method according to an embodiment of the invention, it would additionally be possible to interpret the progression of image intensity as well as additional attributes (spatial coordinates, acquisition parameters, liver volume, blood values such as AFP, bilirubin, etc.) for each individual picture element as a parameter vector. For example, twelve MR contrasts and two examination times for each picture element in the target region would alone yield a 24-dimensional parameter vector. In this way a full analysis is possible, in contrast to the prior art, in which not every picture element is considered, but only the mean value of all the picture elements of a target region, as a result of which spatial information, such as e.g. heterogeneity within the tumor, is lost.

In order to achieve a dimensional reduction, the methods already specified above can again be used, for example a difference calculation can also be used here as a dimensional reduction, whereby e.g. the ADC value at a first point in time less the ADC value at a second point in time is determined and two values within the value tuple are in this way replaced by a difference value so as to reduce the value tuple by a dimension. A further option would be a dimensional reduction to a new basis with fewer dimensions with the aid of a principal component analysis, for example a reduction from three parameters such as ADC, VE, fat fraction to two parameters.

Figure 11:
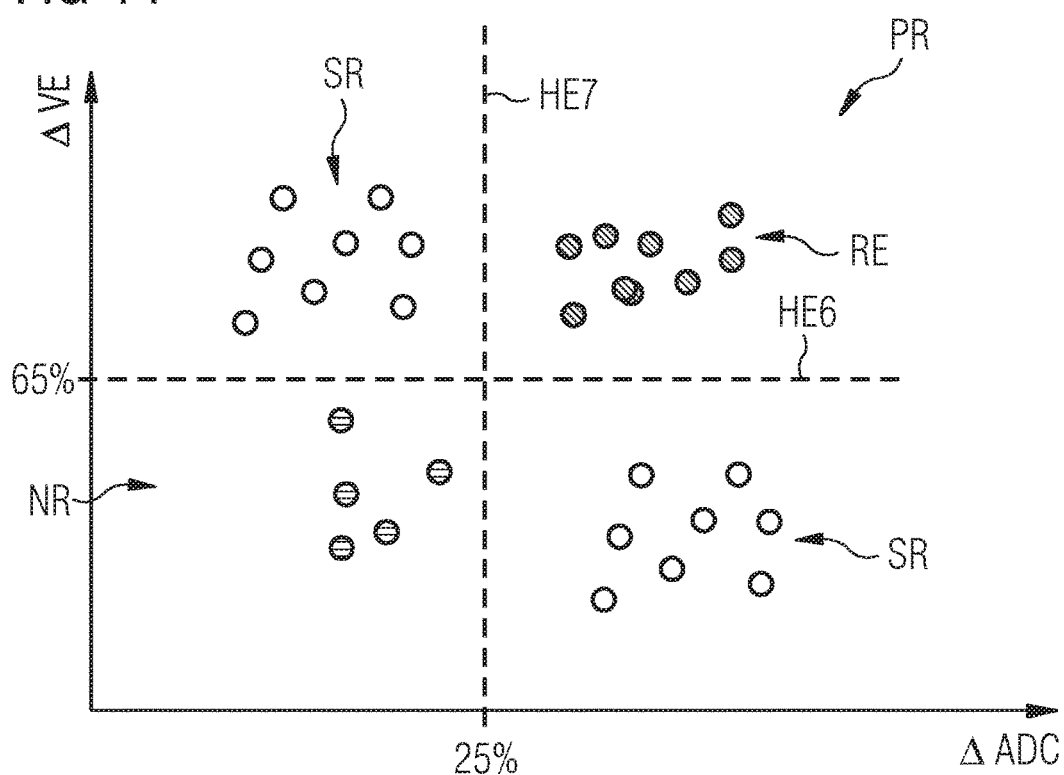
FIG. 11 shows an example of a possible classification with the aid of linear decision boundaries.

Here, too, it is again possible to assign each individual picture element or the entire tumor volume to a particular most probable class among the classes listed above, by comparing e.g. the parameter values or the location of individual value tuples in the high-dimensional parameter space with corresponding value tuples from patients with a known course of treatment. I.e. reference value tuples are referred to here, and in this way a direct classification of the individual picture elements or of a region is carried out. Similarly, certain decision boundaries may be known from previous studies, i.e. hyperplanes which can be used as boundary surfaces or lines, such as, for example, that the ADC value or VE value has changed by at least a certain percentage. Such an example is represented in very simple schematic form in FIG. 11. Plotted here is a parameter space whose one axis comprises the difference of the VE values from the first and second measurements (AVE in %) and on the other axis the difference of the ADC scores from the two measurements (ΔADC in %). Based on known studies, two hyperplanes HE6, HE7—in this image in the form of simple boundary lines—can be determined, which divide the overall space into four quadrants. Depending on which area the value tuples are arranged in, they are to be assigned to one of the classes, namely either the "non-responder" NR class or the "semi-responder" SR class or the "responder" RE class. It is clear that in FIG. 11, only a two dimensional space is shown, because it is simpler to represent. The principle can, however, also be applied to any higher-dimensional spaces. Provided the overall space is of adequately low dimension, however, such decision boundaries can also be visualized as support with the actual data points.

Conversely, visually identified decision boundaries can here, too, again be traced back to simple conventional decision rules. Furthermore, known cluster centers or corresponding probability density distributions can be displayed.

In order to check a possible spatial connection, the user could select a portion of the picture elements labeled e.g. as "non-responder" in the parameter space. This is again possible, for example, by freehand segmentation. These selected data points can then, as described above, be overlaid with a suitable anatomical image as back-mapping in order to label the corresponding picture elements in the anatomical image or in the spatial domain representation. In the process, simultaneous back-mapping of all the data points can be carried out, in which each point is color-coded according to its class affiliation.

Here, too, data analysis with the aid of machine-learning methods is again possible. Preferably, therefore, for example, artificial neural networks are used in order to predict therapeutic success from the observed parameter combinations.

Example 3: Computer-Aided Assessment of Tumor Grades in Prostate Carcinomas

The aim here is to determine the tumor grade in prostate carcinomas through multi-parametric MRT in order in this way to save patients from a possibly unnecessary biopsy or even total resection. In the case of a modified objective, it could automatically be detected in the course of progress monitoring if a previously inconspicuous or benign region is developing into a malignant lesion.

The examination includes here of multiple MR contrasts, usually also including dynamic contrast-enhanced perfusion.

Here, too, the progression of the image intensity of each individual picture element as well as additional attributes, i.e. the spatial coordinates, the acquisition parameter, the prostate volume and blood values such as the PSA, can again be interpreted as parameter vectors. If twelve MR contrasts are performed for each picture element, then here, too, an at least 12-dimensional parameter vector is again produced.

A dimensional reduction can be carried out here simply by calculating for each individual picture element model parameters such as ADC or Ktrans. These parameters are an integral part of established parametric models for the signal curve in diffusion imaging with different diffusion weighting or from the contrast dynamics at different times.

Furthermore, a reduction of the dimensions is also possible here with the aid of a principal component analysis. For example, with the aid of a principal component analysis a reduction from the three parameters ADC, Ktrans, T2 signal intensity to two parameters would be possible.

The grade of the tumor determined with the aid of the method or the probability that a picture element corresponds to a clinically significant tumor can be overlaid color-coded as a new parameter map on the spatial domain or the anatomical image so as to simplify spatial assignment. Equally, a machine-learning method can of course also be used here.

Example 4: Scatter-Plot Analysis of Multi-Parametric Magnetic Resonance Data

One aim here is the early assessment of therapy responses based on multi-parametric magnetic resonance measurements at one or more times in an analogous manner to the second example embodiment.

Here, too, before, during and after therapy, typically various MR contrasts are acquired e.g. twelve volumes in each case. Instead now of working as previously with the aid of average values for the ADC, the VE or similar values for entire areas, the progression of the image intensity of each individual picture element, as well as additional attributes, are now again interpreted within the scope of an embodiment of the invention as parameter vectors. An examination of a total of p parameters then results in an at least p-dimensional value distribution.

In this case, too, a parameter reduction is again possible for individual picture elements, by offsetting particular parameter values against one another—for example differences or ratios are formed—in order in this way to reduce the number of values within a value tuple.

Here, too, a principal component analysis or similar kinds of dimensional reduction are again possible.

Furthermore, the target volume under consideration can also be analyzed here, sub-areas in the parameter space being selected and the value tuples located in this area being labeled e.g. in different colors in a back-mapping process in the original spatial domain or the anatomical image in order in this way to permit a spatial connection between particular value areas of the parameter space and the anatomical image.

In addition, the data may (as incidentally also in all the other examples) also be represented in the form of histograms. An example of this would be a histogram which shows the distribution of the ADC value for the individual picture elements. For example, a change in the histogram distribution from a monomodal distribution with a single peak about a certain ADC value that lies in the range of a typical ADC value for tumor tissue toward higher or lower values (i.e. to a bimodal distribution) would permit the interpretation that more and more picture elements show necrosis, and likewise more and more picture elements have a low ADC value, corresponding to the normal ADC value of bone marrow. The number of picture elements which show a tumor tissue value, on the other hand, is declining. This then indicates that the therapy is being successful.

Such a histogram representation can be evaluated automatically, semi-automatically or, if it can be represented simply, also manually, in order to define particular boundary lines and to assign the individual value tuples for the individual picture elements to particular classes and then to represent this class affiliation again within the scope of a back-mapping to the spatial domain. By this, it can again be shown which spatial areas the therapy is working in. In this way, spatial parameters such as e.g. the spatial center of gravity in the anatomical image, particular contrasts or combinations of contrasts can thus also be checked with regard to their clinical relevance. For example, it is known that peripheral metastases considerably worsen the prognosis by comparison with metastases in the trunk. Within the scope of the method according to an embodiment of the invention, this can be detected more easily than previously.

A major advantage of the method according to an embodiment of the invention is also that automatic analysis of the distribution, e.g. of the heterogeneity, or automatic definition of the number of modes of a histogram or of the number of clusters can speed up clinical interpretation of the data and simplify quantification in order to establish greater objectivity.

Machine-learning methods can be particularly appropriate here. For example, an expectation-maximization algorithm can be used as part of a machine-learning method to specify the modes in a two-dimensional histogram or in a higher-dimensional space for locating clusters. Furthermore, it is again possible to plot or place automatically in a scatter plot (=point cloud) decision boundaries which have previously been learnt with similar clinical objectives with the aid of machine-learning algorithms based on data from other patients.

In combination with automatic organ segmentation, different criteria can, for example, also be applied respectively to each organ and body region in order in this way to structure the diagnosis still further or to represent organ-specific expressions of the distribution of parameters.

In conclusion, it is once again pointed out that the control devices described in detail hereinabove are merely example embodiments, which can be modified by one skilled in the art in a wide variety of ways without departing from the scope of the invention. Furthermore, the use of the indefinite article "a" or "an" does not preclude the possibility that the features concerned may also be present more than once. Likewise, it is not precluded that elements of the present invention designated and/or described as individual units or modules include multiple interacting sub-components which optionally may also be distributed spatially.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining result data based upon medical imaging data of an examination object, the method comprising:
    collecting the medical imaging data having been collected in various measurements from multiple medical images,
    forming a high-dimensional first parameter space in which measurement values of the multiple medical images are represented with aid of value tuples, each of the measurement values of the multiple medical images being assigned to a value tuple of the value tuples at least one of based on a spatial arrangement of a respective measurement value in the examination object;
    analyzing the value tuples in the high-dimensional first parameter space using a mapping function to at least one further parameter space including a relatively lower dimension having reduced value tuples than the high-dimensional first parameter space to determine result data, the mapping function including integrating the value tuples over defined areas of the high-dimensional first parameter space thereby reducing the value tuples to a relatively lower dimension than the high-dimensional first parameter space; and
    outputting the determined result data.

2. The method of claim 1, wherein the various measurements comprise identical measurements at various times.

3. The method of claim 1, wherein, to determine the result data, interim result data is first determined by a first mapping function from the first parameter space to a second parameter space and an analysis is performed on the interim result data;
    wherein the analysis is performed using at least a second mapping function to at least a third parameter space including a relatively lower dimension than the second parameter space; and
    wherein the first mapping function and the second mapping function include different function types.

4. The method of claim 1, wherein the analyzing is performed taking into account positions of the value tuples in a parameter space in relation to a boundary hyperplane of the parameter space.

5. The method of claim 1, wherein the analyzing includes an assignment of the value tuples to value-tuple groups.

6. The method of claim 5, further comprising analyzing an arrangement of a value-tuple group, of the value-tuple groups, in the parameter space.

7. The method of claim 6, wherein the arrangement of the value-tuple group is determined taking into account a collective position of the respective value-tuple group in the parameter space.

8. The method of claim 1, wherein the analyzing of the value tuples is performed taking into account a position in relation to at least one reference value tuple.

9. The method of claim 1, wherein the analyzing of the value tuples includes a segmentation.

10. The method of claim 1, wherein the analyzing includes at least one of morphological operations and filtering.

11. The method of claim 1, further comprising a temporal analysis of a change of value tuples in the parameter space.

12. The method of claim 1, wherein the analyzing includes a machine learning method.

13. The method of claim 1, wherein the outputting includes visualizing of the result data and wherein the visualizing of the result data includes labeling of at least one of picture elements and regions in a spatial domain representation of the examination object, wherein the labeling is performed depending on a result of the analyzing of the value tuples in at least one of the high-dimensional first and a further parameter space.

14. The method of claim 13, wherein the visualizing of the result data includes a visualization of a temporal analysis by at least one of colors and vectors.

15. A device for determining result data based upon medical imaging data of multiple medical images of an examination object, the medical imaging data having been collected in various measurements, the device comprising:
   at least one processor, the at least one processor being configured to:
   form a high-dimensional first parameter space in which measurement values of the multiple medical images are represented with aid of value tuples, each the measurement values of the multiple medical images being assigned to a value tuple of the value tuples at least one of based on a spatial arrangement of a respective measurement value in the examination object;
   analyze the value tuples in the high-dimensional first parameter space using a mapping function to at least one further parameter space including a relatively lower dimension having reduced value tuples than the high-dimensional first parameter space to determine result data, the mapping function including integrating the value tuples over defined areas of the high-dimensional first parameter space thereby reducing the value tuples to a relatively lower dimension than the high-dimensional first parameter space; and
   output the determined result data.

16. A non-transitory computer program product including a computer program, directly loadable into a storage device of computer unit, including program sections for executing the method of claim 1 when the computer program product is executed in the computing unit.

17. A non-transitory computer-readable medium including program sections, readable and executable by a computer unit, to execute the method of claim 1 when the program sections are executed by the computer unit.

18. The method of claim 1, wherein the medical imaging data was collected in various measurements with different measurement devices.

19. The method of claim 1, wherein the outputting includes visualization of the determined result data.

20. The method of claim 2, wherein the mapping function further includes at least one of the following:
   mapping to a color space,
   mapping to discrete classes,
   mapping to a space with clinically relevant semantic coordinate axes, and
   mapping to a system of coordinates with mathematical characteristics.

21. The method of claim 1, wherein, to determine the result data, interim result data is first determined by a first mapping function from the first parameter space to a second parameter space and an analysis is performed on the interim result data;
   wherein the analysis is performed using at least a second mapping function to at least a third parameter space including a relatively lower dimension than the second parameter space; and
   wherein the first mapping function and the second mapping function include different function types.

22. The method of claim 4, wherein the analyzing includes an assignment of the value tuples to value-tuple groups.

23. The method of claim 22, further comprising analyzing an arrangement of a value-tuple group, of the value-tuple groups, in the parameter space.

24. The method of claim 23, wherein the arrangement of the value-tuple group is determined taking into account a collective position of the respective value-tuple group in the parameter space.

25. The method of claim 11, wherein the temporal analysis includes a temporal shift of individual value tuples.

26. The method of claim 13, wherein the visualizing of the result data includes a visualization of a temporal analysis by at least one of colors and vectors.

27. The device of claim 15, wherein the medical imaging data was collected in various measurements with different measurement devices.

28. The device of claim 15, wherein the output includes visualization of the determined result data.

29. The method of claim 1, wherein the a dimension of the value tuples is reduced by the mapping function to the at least one further parameter space.

* * * * *